United States Patent [19]
Witzel

[11] 4,367,747
[45] Jan. 11, 1983

[54] PNEUMATIC DILATATOR FOR INTRODUTION INTO THE ESOPHAGUS

[76] Inventor: Lothar Witzel, Hangweg 8 A, D-1000 Berlin 28, Fed. Rep. of Germany

[21] Appl. No.: 193,071

[22] Filed: Oct. 1, 1980

[51] Int. Cl.$^3$ ............................................. A61M 29/08
[52] U.S. Cl. ........................................ 128/344; 128/8; 604/79; 604/99; 604/100
[58] Field of Search ................. 128/344, 343, 349 B, 128/349 BV, 4, 8, 242

[56] References Cited

U.S. PATENT DOCUMENTS

| | | | |
|---|---|---|---|
| 1,598,284 | 8/1926 | Kinney | 128/344 |
| 2,043,083 | 6/1936 | Wappler | 128/344 |
| 3,882,852 | 5/1975 | Sinnreich | 128/4 |
| 4,064,882 | 12/1977 | Johnson | 128/349 BV X |
| 4,198,981 | 4/1980 | Sinnreich | 128/344 |

Primary Examiner—Stephen C. Pellegrino
Attorney, Agent, or Firm—Spellman, Joel and Pelton

[57] ABSTRACT

A pneumatic dilatator for introduction into the esophagus and for treatment of a constricted segment of the intestinal system of a living being contains an inflatable balloon and a tube of a given length which is passed through the balloon. The tube receives a gastroscope for observation during treatment. The balloon is preferably of cylindrical shape. Preferably it consists of a flexible material of little elasticity, such as polyurethane, which limits its diameter during an inflation to a given upper value.

6 Claims, 1 Drawing Figure

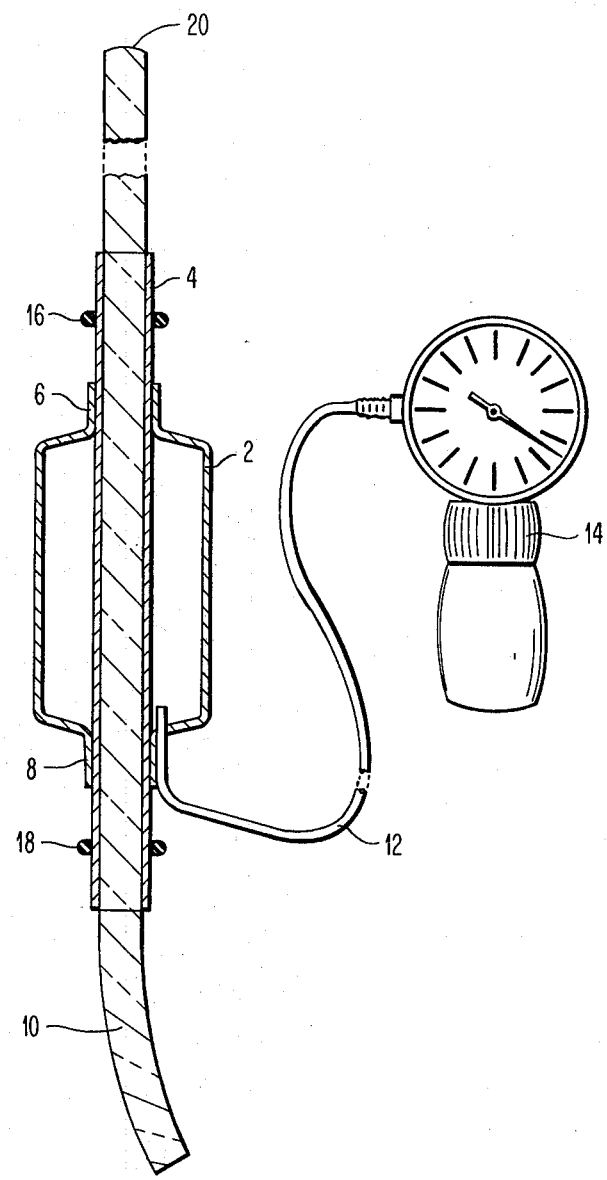

PNEUMATIC DILATATOR FOR INTRODUTION INTO THE ESOPHAGUS

FIELD OF THE INVENTION

This invention relates to a pneumatic dilatator for introduction into the esophagus of a living being, and for widening a constricted segment, said segment being either a part of the esophagus or a part of the intestinal system connected therewith. Particularly, this invention relates to the treatment of achalasia in man. Still more particularly, this invention relates to a dilatator having an inflatable balloon whose diameter is limited during the inflation in the constricted segment to an upper limiting value.

BACKGROUND OF THE INVENTION

In achalasia, the inlet of the stomach, the cardia, is constricted. Food remains in the esophagus, which thus can considerably distend. The treatment of achalasia consists, in addition to other methods, in pneumatic dilatation (Nanson, E. M., Gastroenterology 51, pp. 236-241, 1966; Vantrappen, G., Hellemans, J., Deloof, W., Valembois, P., Vandenbroucke, Gut 12, pp. 268-275, 1971; Wienbeck, M., Heitman, P., Dtsch. Med. Wschr. 98, pp. 814-825, 1973). Pneumatic dilatation is characterized by its simplicity and high success rate.

In pneumatic dilatation, an inflatable balloon is introduced into the esophagus of man. It is pushed into the constricted segment, for instance, the cardia, and is inflated there to widen the constriction. It is necessary to limit the diameter of the balloon to an upper value so that the balloon does not assume too great dimensions above and/or below the constricted segment in the esophagus or stomach. With a known pneumatic dilatator this is achieved by surrounding the balloon, which can be inflated from the outside of the human body, by a cloth bag. This cloth bag in turn is surrounded by a protective balloon. The cloth bag limits the dilatator to a certain diameter during the inflation.

The presently known balloon dilatators have a number of disadvantages. First of all, the manufacturing process of a dilatator, consisting of three layers (balloon, cloth bag, balloon), is rather elaborate and expensive. Particularly the incorporation of the cloth bag can lead to complications. In addition, such a dilatator may be rather sensitive to damage. Under certain circumstances, problems may also arise in cleaning and re-use. Finally, it is a significant disadvantage that the known dilatators are not introduced and dilated under the direct supervision of a physician, but by an indirect control method, namely under X-ray control. In the blind introduction of the instrument, perforations and thus unfortunate complications occur in 2 to 9% of all cases, as observations have shown.

In the advanced stage of achalasia with a twisted esophagus, it is usually not possible to push the dilatator of the known design into the constricted cardia. This difficulty has been overcome, in certain circumstances, by letting the patient swallow a guide thread on the day preceding this treatment, the thread being weighted with a bag containing a contrast medium, such as barium sulfate, which may be seen in X-ray pictures. For dilatation, the guide thread, which has advanced into the lower intenstinal segment, is tightened, and a flexible guide wire is pushed along it. The dilatator is then introduced over this guide wire. It can be readily seen that such a procedure is inconvenient both for the physician and for the patient.

SUMMARY OF THE INVENTION

Objects

It is an object of this invention to design a dilatator of the above described type which can easily be handled by a physician.

It is another object of this invention to provide a pneumatic dilatator for introduction into the esophagus, for which the risk of perforation is substantially reduced.

It is still another object of this invention to provide a pneumatic dilatator which can be used for treatment even of the advanced stage of achalasia.

It is still another object of this invention to provide a pneumatic dilatator which can be re-used a multitude of times.

Summary

According to this invention the pneumatic dilatator contains an inflatable balloon and a tube of a given length which is passed through the balloon. The tube is provided to pass a gastroscope through it during treatment of a constriction. Thus, the dilatator can be introduced into the constricted segment, for example the cardia, under observation through the gastroscope. The dilatation, too, can be performed under observation. Therefore the risk of perforation of the esophagus is practically completely eliminated in the pneumatic treatment of achalasia or any other disease characterized by a constricted segment of the intestinal system of a living being.

In order to be able to manufacture the dilatator without major difficulties, the balloon may consist of a flexible material of little elasticity, according to a particularly preferred embodiment of the invention. Such material may comprise polyurethane.

In the dilatator according to the invention the balloon thus does not consist of several layers, but is made in one piece of a homogeneous material. This material itself ensures the limitation of the balloon diameter, as soon as the balloon is inflated in the constricted segment. A cloth bag for the limitation thus does not have to be provided. This facilitates considerably the manufacture of the dilatator and also reduces the costs.

As just mentioned, it is of particular advantage if the balloon is made of polyurethane or a material containing polyurethane. Such a material is extremely rugged and stable. It should also be stressed that such a dilatator is easy to clean after use. Particularly good results regarding the ease of manufacture, handling, and safety are obtained if the balloon is composed as follows: polyurethane=polyether-IU of the Estane type, made by Goodrich Co., Cleveland, Ohio, USA. For strengthening the wall, PVC resin may be added as needed, for instance the type Lonzavyl S 582 by Lonza AG, Basel, Switzerland.

A special advantage of the dilatator according to the invention is that is can be readily built of elements which are commercially available.

The foregoing and other objects, features and advantages of the invention will be apparent from the following more particular description of preferred embodiments of the invention, as illustrated in the accompanying drawings.

BRIEF DESCRIPTION OF THE DRAWING

The drawing shows in a partially cross sectional view a pneumatic dilatator for the treatment of achalasia in man, which is fixed on a gastroscope.

DETAILED DESCRIPTION OF THE PREFERRED EMBODIMENTS

The main part of the dilatator is an inflatable balloon 2, through which a flexible tube 4 is passed in an airtight manner. The balloon 2 is cylindrical. It consists of a flexible material, which expands only little during inflation. Preferably, it consists of polyurethane with a PVC-resin admixture. In the non-inflated state, the balloon can be folded down onto the tube 4. The tube 4 is passed through the two end faces of the cylindrical balloon, and the end faces are extended to the outside by tubular lugs 6 and 8. In the range of these lugs the balloon 2 is secured on the tube 4 in airtight fashion. For example, the balloon 2 and the tube 4 can be melted together or glued to each other in the range of the lugs 6 and 8. The thickness of the polyurethane sheet is between 0.3 and 0.8 mm. The length of the balloon 2, measured in the direction of tube 4, is about 150 mm.

The diameter of the balloon 2 in the flat state at 0 mm Hg internal excess pressure is about 13 mm. The use of the material polyurethane has the effect that the width of the balloon 2 in the inflated state is limited to about 40 mm at an internal excess pressure of 300 mmHg. It was found in the examination of patients that this pressure and this width are highly suitable for extending the cardia. In contrast to conventional dilatators, no cloth bag is provided here. Its function is taken over by the polyurethane. It was also found in the mentioned examinations that, with an internal balloon pressure of 300 mmHg during the dilatation, a sufficient expansion pressure acts in the constricted segment, without the balloon 2 assuming destructive dimensions above and below the cardia in the esophagus and stomach.

The tube 4 is made of a material which is at least slightly flexible. In particular, the tube 4 may consist of polyvinyl-chloride (PVC). Its interior is designed to receive a gastroscope 10, which is an endoscope for viewing the esophagus and the stomach, of small diameter. In order to match the outside diameter of the gastroscope 10, the tube 4 may have an inside diameter of 10 mm, for example. It may then have an outside diameter of 11 mm. The above mentioned tests have shown that such a tube 4 should have a length of about 20 cm. A length of 15 cm will still produce good results.

Into balloon 2 opens a small tube or flexible inflation pipe 12, through which the balloon 2 can be inflated from the outside. The capillary tube 12 may have a thickness of 5 to 6 mm and a length of about 60 mm. It is pneumatically connected with a commercial blood pressure manometer 14 having a rubber squeeze bulb. The blood pressure manometer 14 makes it possible to inflate the balloon 2 in situ to an internal excess pressure of 300 mm Hg, for example, and to control and maintain this excess pressure for some time. For reasons of durability it is advisable if the tube 12 opens into the balloon 2 on the rear cylinder face close to the tube 4, as shown.

As can be seen from the drawing, the flexible tube 4 is pushed over the gastroscope 10. The gastroscope 10 can be a commercially available small-caliber endoscope with direct vision. The two ends of the tube 4 are somewhat cut-in in longitudinal direction, so that they terminate in a star (not visible in the drawing). Over each end is pushed a rubber ring 16 and 18, which retains the end on the gastroscope 10. By means of these rubber rings 16 and 18, the balloon 2 can be detachably fixed at any point of the gastroscope 10. The above-mentioned tests have shown that the center of the balloon 2 should be arranged in many cases preferably about 20 cm from the tip 20 of the gastroscope 10.

During treatment the tip 20 of the gastroscope 10 (pointing upward in the drawing) with the attached balloon 2 is introduced through the mouth of the patient into the esophagus. Looking through gastroscope 10, the physician will advance the dilatator through the cardia into the stomach. By reversing the direction of the instrument tip 20 in the stomach, the dilatator can be so placed—likewise under observation—that the narrow segment encloses the center of the balloon 2. The known placement difficulties in the "blind" introduction of the dilatator are thus avoided. Under observation, the balloon 2 is inflated from the outside by means of the blood pressure manometer 14. If pains should start, the air is let out, and after waiting for about a minute, the balloon 2 is inflated again until an internal excess pressure of about 300 mmHg can be maintained for about 2 minutes. The cardia is spread by the dilatation of the balloon 2. Since the material polyurethane does not markedly expand at an excess pressure of 300 mmHg in the balloon 2, and the width of the balloon 2 in the inflated state is limited to about 40 mm, no over-extension of the esophagus is possible.

Since both the placement and the dilatation are effected under the visual control of the physician, there is no risk of perforation of the esophagus with proper handling. Furthermore the dilatator according to the invention can be used even with an S-shaped mega-esophagus. Here, too, a simple and effective visual control in the introduction and placement is possible.

Tests with balloon diameters of 30 mm, 35 mm and 40 mm have shown that a single balloon size suffices for adult patients, even in several successive sessions. Of particular advantage is the above-mentioned size of about 40 mm.

The pneumatic dilatator represented in the drawing is extremely stable. The above-mentioned tests have shown that it can be inflated over 1000 times without any mechanical changes.

Cleaning is very simple. The dilatator is first washed with warm water and soap, and then gas-sterilized.

While the form of the pneumatic dilatator herein described constitutes a preferred embodiment of the invention, it is to be understood that the invention is not limited to this precise form of assembly, and that a variety of changes may be made therein without departing from the scope of the invention.

What is claimed is:

1. A pneumatic dilatator for introduction into the esophagus and for treatment of a constricted segment of the intestinal system of a living being, comprising in combination:
   (a) an inflatable balloon of generally cylindrical shape having two cylinder end faces opposed to each other, said balloon consisting throughout of a flexible material of small elasticity, thereby limiting the diameter of said balloon to a given upper value of approximately 40 mm when said balloon is inflated in said constricted segment at an internal excess pressure of approximately 300 mmHg;
   (b) a tube of a flexible material having a given length, said tube being passed through said balloon and said balloon being secured thereon in the range of said cylinder end faces, said balloon thereby extending along said tube at a length of approximately 150 mm;

(c) a gastroscope passed through said tube for visual control of the introduction of the dilatator into said constricted segment and/or of an inflation of said balloon;

(d) means for detachably mounting said tube on said gastroscope;

(e) a flexible inflation pipe opening into said balloon; and (f) a blood pressure manometer including a squeeze bulb connected to said inflation pipe for inflating said balloon when positioned in said constricted segment.

2. The dilatator according to claim 1, wherein said tube is made of polyvinyl chloride.

3. The dilatator according to claim 1, wherein said tube is displaceably mounted on said gastroscope by means of two rubber rings placed on respective ends of said tube.

4. The dilatator according to claim 1, wherein the center of said balloon is located about 20 cm from the tip of said gastroscope.

5. The dilatator according to claim 1, wherein said inflation pipe is about 5 mm thick and about 60 mm long.

6. The dilatator according to claim 1, wherein said inflation pipe opens into said balloon next to said tube.

* * * * *